US006964773B1

(12) United States Patent
Morrison

(10) Patent No.: US 6,964,773 B1
(45) Date of Patent: Nov. 15, 2005

(54) TRANSFER RESISTANT ANHYDROUS COSMETIC COMPOSITION

(75) Inventor: Sam B. Morrison, Clark, NJ (US)

(73) Assignee: L'Oreal S.A., Paris (FR)

( * ) Notice: Subject to any disclaimer, the term of this patent is extended or adjusted under 35 U.S.C. 154(b) by 18 days.

(21) Appl. No.: 09/717,204

(22) Filed: Nov. 22, 2000

(51) Int. Cl.[7] .......................... A61K 6/00; A61K 7/021; A61K 31/74

(52) U.S. Cl. ...................... 424/401; 424/63; 424/78.03

(58) Field of Search ........................ 424/401, 63, 78.03

(56) References Cited

U.S. PATENT DOCUMENTS

| | | |
|---|---|---|
| 3,827,999 A | 8/1974 | Crossland |
| 3,867,533 A | 2/1975 | Schmolka |
| 4,164,563 A | 8/1979 | Chang |
| 4,369,284 A | 1/1983 | Chen |
| 4,425,328 A | 1/1984 | Nabial |
| 4,528,390 A * | 7/1985 | Kimura ...................... 556/450 |
| 4,716,183 A | 12/1987 | Gamarra et al. |
| 4,798,853 A | 1/1989 | Handlin, Jr. |
| 4,944,937 A | 7/1990 | McCall |
| 4,976,961 A | 12/1990 | Norbury et al. |
| 4,976,963 A | 12/1990 | Schricker et al. |
| 5,013,473 A | 5/1991 | Norbury et al. |
| 5,102,656 A | 4/1992 | Kasat |
| 5,152,991 A | 10/1992 | Vogel et al. |
| 5,169,626 A | 12/1992 | Tanner et al. |
| 5,221,534 A | 6/1993 | DesLauriers et al. |
| 5,232,689 A | 8/1993 | Katsoulis et al. |
| 5,254,332 A | 10/1993 | Grezcyn et al. |
| 5,294,438 A | 3/1994 | Chang et al. |
| 5,302,381 A | 4/1994 | Greczyn et al. |
| 5,510,072 A | 4/1996 | Rosenqvist et al. |
| 5,539,021 A | 7/1996 | Pate et al. |
| 5,558,872 A | 9/1996 | Jones et al. |
| 5,578,299 A | 11/1996 | Starch |
| 5,688,842 A | 11/1997 | Pate, III et al. |
| 5,690,920 A | 11/1997 | Dubief |
| 5,710,206 A | 1/1998 | Francis et al. |
| 5,711,940 A | 1/1998 | Kuentz et al. |
| 5,756,082 A | 5/1998 | Cashin et al. |
| 5,800,816 A | 9/1998 | Brieva et al. .................. 424/63 |
| 5,851,517 A | 12/1998 | Mougin et al. |
| 5,928,632 A * | 7/1999 | Reusch ..................... 424/78.03 |
| 5,945,095 A * | 8/1999 | Mougin et al. .......... 424/78.02 |
| 5,959,009 A | 9/1999 | Konik et al. |
| 6,060,072 A | 5/2000 | Konik et al. ................ 424/401 |
| 6,066,313 A * | 5/2000 | Anton et al. ................... 424/63 |
| 6,074,654 A | 6/2000 | Dreschsler et al. ......... 424/401 |
| 6,248,339 B1 * | 6/2001 | Knitowski et al. ........... 424/401 |
| 6,464,969 B2 | 10/2002 | De La terie et al. |

FOREIGN PATENT DOCUMENTS

| | | |
|---|---|---|
| EP | 0 154 831 A2 | 9/1985 |
| EP | 0 299 718 | 1/1989 |
| EP | 0 154 831 B1 | 12/1990 |
| EP | 0 497 144 B1 | 9/1995 |
| EP | 0 749 746 B1 | 9/1997 |
| EP | 0 850 649 A1 | 7/1998 |
| EP | 0 925 780 A1 | 6/1999 |
| EP | 1 002 528 A1 | 5/2000 |
| EP | 1 163 896 A1 | 12/2001 |
| FR | 2 357 244 | 2/1978 |
| FR | 2 710 646 | 4/1995 |
| JP | 53-094041 | 8/1978 |
| JP | 58-160381 | 9/1983 |
| JP | 62-249653 | 10/1987 |
| JP | 4-50234 | 2/1992 |
| WO | WO 88/01164 | 2/1988 |
| WO | WO 91/13839 | 9/1991 |
| WO | WO 94/12190 | 6/1994 |
| WO | WO 97/17058 | 5/1997 |
| WO | WO 97/17059 | 5/1997 |
| WO | WO 97/49352 | 12/1997 |
| WO | WO 98/38981 | 9/1998 |
| WO | WO 98/42298 | 10/1998 |
| WO | WO 99/22710 | 5/1999 |
| WO | WO 99/22711 | 5/1999 |
| WO | WO 99/28429 | 6/1999 |
| WO | WO 00/26285 | 5/2000 |
| WO | WO 00/49997 | 8/2000 |

OTHER PUBLICATIONS

English language Derwent Abstract of JP 53-094041, Aug. 1978.
Abstract 114: 108 976, XP002143304, "Film-forming Aerosol Preparations Containing ABA-type Triblock Thermoplastic Elastomers."
English Language Abstract of EP 0 925 780 A1, Jun. 1999.
English Language Abstract of EP 1 002 528 A1, May 2000.
International Search Report dated Oct. 8, 2000.
Co-Pending U.S. Appl. No. 09/258,809; filed Feb. 26, 1999, Inventors Carolyn Caes et al. For: Cosmetic Compositions Containing Di-Block, Tri-Block, Multi Block and Radial Block Copolymers.
Copy of International Search Report in PCT/US01/43212, mailed Jan. 27, 2001.

* cited by examiner

*Primary Examiner*—Shengjun Wang
(74) *Attorney, Agent, or Firm*—Finnegan, Henderson, Farabow, Garrett & Dunner LLP

(57) ABSTRACT

A composition with transfer resistance and/or waterproof properties comprising at least one linear dimethicone; and at least one block copolymer film former chosen from tri-block copolymer film formers, multi-block copolymer film formers and radial block copolymer film formers. The invention also provides for a cosmetic powder delivery system and a method of delivering a powder composition to a keratinous substance.

31 Claims, No Drawings

TRANSFER RESISTANT ANHYDROUS COSMETIC COMPOSITION

The present invention relates to a composition, in one embodiment a cosmetic composition, with transfer resistance and/or waterproof properties, which may also be comfortable to wear. The composition comprises at least one linear dimethicone; and at least one block copolymer film former chosen from tri-block copolymer film formers, multi-block copolymer film formers and radial block copolymer film formers. The invention also provides for a cosmetic powder delivery system and a method of delivering a powder composition to a keratinous substance.

Many cosmetic compositions, including pigmented cosmetics such as foundations, concealers, mascaras, lipsticks, and other cosmetic and sunscreen compositions, have been developed for longer wear and non transfer properties. For example, cosmetic foundations are very popular and it is desirable to have a foundation that is long lasting and does not wear off easily. This is usually accomplished by the use of compositions which form a film after application. Such compositions generally contain volatile solvents which evaporate on contact with the skin or other keratinous tissue, leaving behind a layer composed essentially of waxes and/or resins, pigments, fillers and actives.

However, these compositions tend to be uncomfortable for the wearer as the composition remains on the skin or other keratinous tissue as a brittle or non-flexible film. There is also a tendency for the composition to flake off because of poor adherence on the skin or other keratinous tissue. Furthermore, many of these compositions tend to be tacky, resulting in poor application and spreadability characteristics.

The need therefore still remains for improved long-wearing cosmetic compositions which transfer little or not at all, i.e., "transfer free" or transfer resistant compositions which also possess good cosmetic properties such as comfort and water resistance and which are non tacky and non "draggy" during and after application.

The present invention makes it possible to obtain one or more of the following properties: excellent adherence to the substrate to which it is applied, flexibility, wearability, good drying time, good retention, transfer resistance, and water resistance. In one embodiment, the invention provides a composition comprising at least one linear dimethicone and at least one block copolymer film former chosen from tri-block copolymer film formers, multi-block copolymer film formers and radial block copolymer film formers.

The invention also provides for a cosmetic delivery system comprising at least one linear dimethicone; at least one block copolymer film former chosen from tri-block copolymer film formers, multi-block copolymer film formers and radial block copolymer film formers; and at least one cosmetic powder.

In another embodiment, the invention provides a method of delivering a powder composition to a keratinous substance comprising applying to said keratinous substance a composition comprising at least one linear dimethicone; at least one block copolymer film former chosen from tri-block copolymer film formers, multi-block copolymer film formers and radial block copolymer film formers; and at least one cosmetic powder.

It is to be understood that both the foregoing general description and the following detailed description are exemplary and explanatory only and are not restrictive of the invention as claimed.

The composition of the invention as set forth above, comprises at least one linear dimethicone and at least one block copolymer film former chosen from tri-block, multi-block and radial block copolymer film formers. In one embodiment, the composition of the invention may be a foundation and may include, for example, additional ingredients chosen from powders, pigments, sunscreens, and skin protectant coatings. The composition may deliver the additional ingredients, for example a powder composition, to the surface of the skin. For example, the powder may be delivered wet and/or creamy and rendered transfer resistant by reduction of the volatile ingredients. The result on the skin may be a dry, transfer resistant powder.

In other embodiments, the compositions of the invention may be chosen from molded and poured cosmetics and cosmetic sticks. Other examples of forms in which the compositions of the invention may exist include eyeshadow, eyeshadow base, blush, lipstick, fragrance delivery system, deodorant stick, skin protectant stick, sunscreen stick, medication cream or other medication application system, adhesive or insect repellent. In another embodiment, the composition is a base for a cosmetic powder. For example, the composition may be applied to the skin as a base and the cosmetic powder is then applied to the base.

In one embodiment, the at least one linear dimethicone is a mixture of fully methylated linear siloxane polymers end blocked with trimethylsiloxy units. The at least one linear dimethicone may, for example, be chosen from linear polydimethylsiloxanes. Linear polydimethylsiloxanes are generally of the formula

$(CH_3)_3Si-O-(-Si(CH_3)_2-O-)_n-Si(CH_3)_3$.

In one embodiment, n ranges from 0 to 7. Linear polydimethylsiloxanes are available from various sources including Dow Corning Corporation and General Electric. For example in one embodiment, the polydimethylsiloxanes is chosen from a Dow Corning 200® fluid, which are polydimethylsiloxane polymers sold with average kinematic viscosities ranging from 1.5 cs to 5.0 cs. Other linear dimethicones include, for example, Abil-10-100000 (Goldschmidt), AF 9020 (General Electric), Baysilone Fluids M (Miles) DM Fluids (Shin Etsu), and Wacker Silicone Fluid AKF (Wacker-Chemie). In one embodiment, the linear dimethicone is a dimethicone crosspolymer (for example, Dow Corning® 2-9040 and see U.S. Pat. No. 5,654,362, the disclosure of which is hereby incorporated by reference).

In another embodiment, the at least one linear dimethicone may be chosen from, for example, dimethicone copolyols such as dimethicone copolyol, dimethicone copolyol acetate, dimethicone copolyol adipate, dimethicone copolyol almondate, dimethicone copolyolamine, dimethicone copolyol butyl ether, dimethicone copolyol laurate, dimethicone copolyol stearate; and dimethicone derivatives such as dimethicone silylate, dimethicone propylethylenediamine behenate.

The at least one block copolymer film former of the present invention is chosen from tri-block copolymer film formers, multi-block copolymer film formers and radial block copolymer film formers. A block copolymer film former generally contains at least two thermodynamically incompatible segments. For example, a tri-block is usually defined as an A-B-A type copolymer or a copolymer having soft and hard segments in a ratio of one hard, one soft, and one hard segment. A multiblock, radial or star copolymer film former usually contains any combination of hard and soft segments, provided that there are both hard and soft characteristics. An example of a hard block copolymer segment is styrene, while examples of soft block copolymer segments include ethylene, propylene, and butylene or combinations thereof.

In one embodiment, at least one block copolymer film former of the present invention is chosen from the class of Kraton® rubbers (Shell Chemical Company) or from similar gelling agents. In a further embodiment, the copolymer film former comprises Kraton® rubbers that are present in a gel in amounts ranging from 10 to 20% concentration by weight. Kraton® rubbers may be thermoplastic elastomers in which the polymer chains comprise a tri-block or radial or star block configuration or numerous mixtures thereof. The Kraton® tri-block rubbers have polystyrene segments on each end of a rubber segment, while the Kraton® radial or star configuration may be a four-point or other multipoint star made of rubber with a polystyrene segment attached to each end of a rubber segment. The configurations of each of the Kraton® rubbers form separate polystyrene and rubber domains.

Each molecule of Kraton® rubber is said to comprise block segments of styrene monomer units and rubber monomer and/or co-monomer units. The most common structure for the Kraton® triblock copolymer is the linear A-B-A block type styrene-butadiene-styrene, styrene-isoprene-styrene, or styrene-ethylenebutylene-styrene. The Kraton® rubber configuration is well known in the art and any block copolymer film former with a similar configuration is within the practice of the invention.

Other embodiments include the use of block copolymer film formers comprising a styrene/butylene/ethylene/styrene copolymer (tri-block), an ethylene/propylene/styrene copolymer (radial or star block) or a mixture or blend of the two. (Some manufacturers refer to block copolymers as hydrogenated block copolymers, e.g., hydrogenated styrene/butylene/ethylene/styrene copolymer (tri-block) or hydrogenated ethylene/propylene/styrene copolymer (radial or star block), all of which are within the scope of the invention.) Specific examples include Versagel M5960 or Versagel M5970, which are available from Penreco of Houston Tex., and block copolymers available from Brooks Industries, such as Gel Base.

The at least one block copolymer film former may, for example, be formulated by dissolving the block copolymer in a hydrocarbon solvent. Hydrocarbons useful in the practice of the invention, in one embodiment, may be chosen from mineral oils, mineral solvents, mineral spirits, petroleum, waxes, synthetic hydrocarbons, animal oils, vegetable oils, and mixtures of various hydrocarbons. In one embodiment, the at least one block copolymer film former is formulated by dissolving a block copolymer in isododecane or a light paraffinic solvent. In another embodiment, at least one block copolymer film former may be formulated by dissolving a block copolymer in a non-hydrocarbon solvent such as amyl acetate, butyl acetate, isobutyl acetate, ethyl acetate, propyl acetate or isopropyl acetate.

The solvent and solubility conditions for formulating a block copolymer film former from a block copolymer may be chosen by a person skilled in the art in order to prepare a composition which has the desired properties. One of ordinary skill in the art will be able to determine the solubility parameters and choose a solvent based on the block copolymer chosen for the envisaged application. More information regarding solubility parameters and solvents useful in the processing of specific block copolymers is available from the various manufacturers of block copolymers, e.g., Shell Chemical Company. Additional discussions of polymer solubility parameter concepts are presented in: Encyclopedia of Polymer Science and Technology, Vol.3, Interscience, New York (1965) and Encyclopedia of Chemical Technology, Supp. Vol., Interscience, New York (1971), the disclosures of which are hereby incorporated by reference.

Preferably, the at least one block copolymer film former of the present invention is water insoluble, can be processed at room temperature, offers excellent adherence to the skin, and is tack free.

Depending on the application, the concentration of the at least one linear dimethicone and the at least one block copolymer film former may vary considerably. One of skill in the art will be able to determine routinely the preferred concentration of the at least one linear dimethicone and the at least one block copolymer film former depending on the application and the properties desired.

In one embodiment, the concentration of at least one block copolymer film former ranges from 0.139% to 4.185% by weight, such as from 0.265% to 1.953% by weight. The concentrations as used herein refer to the concentration of active ingredients. The concentration of at least one linear dimethicone, for example, ranges from 25% to 75% by weight, such as from 42% to 54% by weight.

The cosmetic compositions of the invention may further comprise at least one cyclic dimethicone. A cyclic dimethicone, which also may be referred to as a cyclomethicone, generally has the formula

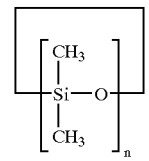

In one embodiment, n has a value of 1 to 7. The at least one cyclic dimethicone is also available from various sources including Dow Corning Chemical. For example in one embodiment, the cyclic dimethicone is chosen from Dow Corning 244® fluid, 245® fluid, 344® fluid, and 345® fluid. Other cyclic dimethicones include, for example, Abil K 4 (Goldschmidt), SF-1204 (General Electric), Baysilone COM 10,000 and 20,000 (Miles) KF994 and KF9945 (Shin Etsu), and Wacker-Belsil CM 020, CM 030, and CM 040 (Wacker-Chemie).

In another embodiment, the compositions of the invention may further comprise at least one additional silicone resin. The at least one additional silicone resin may be chosen from, for example, silanes, siloxanes, siloxysilicates and silsesquioxanes. An example of a siloxane useful in such compositions is polydimethylsiloxane (PDMS), which is usually composed of long straight chains of $(CH_3)_3SiO_{1/2}$ (M units) with varying viscosities depending on the size of the chain or the type of substituent. An exemplary siloxysilicate is trimethylsiloxysilicate, which is represented by the following formula: $[(CH_3)_3—Si—O]_x—(SiO_{4/2})_y$ (MQ Units) where x and y can have values between 50 and 80. Trimethylsiloxysilicates may be chosen from, for example, SR 1000, 554230, or SS4267 available from GE Silicones. Silsesquioxanes, on the other hand, are represented by the following formula: $(CH_3SiO_{3/2})_x$ (T Units) where x has a value of up to several thousand. In one embodiment, the silsesquioxane is chosen from polymethylsilsesquioxanes. A polymethylsilsesquioxanes is a silsesquioxane that does not have substituents replacing the methyl groups. These silicone resins, for example, may be soluble or dispersible in volatile silicones or other organic liquids. In one embodiment, the at least one silicone resin, such as trimethylsiloxysilicate, is dispersed in a linear dimethicone or cyclic dimethicone. The organic liquids may be chosen from, for example, alcohols such as ethanol, isododecane, and isopar E.

In another embodiment, the compositions of the present invention may include at least one powder material. The at least one powder material, for example, may be chosen from talcs; solid polymers including copolymers, such as, polyethylene, PTFE, acrylates copolymer, ethylene acrylate copolymer, and PMMA; nylon, silicas, silk, vegatable flours, starches, pigments, fillers, pearling agents and any cosmetic powder. In one embodiment, the at least one powder material is chosen from polyvinylidene copolymers such as Expancel DE 551 or microbubbles. In another embodiment, the concentration of the at least one powder material ranges from 0.1% to 50% by weight.

Representative pigments include white, colored, mineral, organic, coated and uncoated pigments. Representative mineral pigments include titanium dioxide, optionally surface-treated, zirconium oxide, cerium oxide, iron oxides, chromium oxides, manganese violet, ultramarine blue, chromium hydrate and ferric blue. Representative organic pigments include carbon black, pigments of D & C type, and lakes based on cochineal carmine, barium, strontium, calcium and aluminum. In one embodiment, the pigments may be treated with ITT (isopropyl titanium titanate or triiso stearate).

Fillers should be understood to mean lamellar or non-lamellar, inorganic or synthetic, colorless or white particles. Pearling agents should be understood to mean irridescent particles produced especially by certain mollusks in their shell or else synthesized. Pearling agents that may be used in the practice of the invention include mica, iron oxides, titanium dioxide and any other pearling agent known in the cosmetic arts.

In another embodiment, at least one additional film former may be used. The at least one additional film former may improve smoothness or spreadability, water-resistance, transfer resistance properties, or other cosmetic or pharmaceutical properties desired by one of skill in the art. The at least one additional film former may be chosen from, for example, vinylpyrrolidone/vinyl acetate (PVP/VA) copolymers such as the Luviskol® VA grades (all ranges) from BASF® Corporation and the PVP/VA series from ISP; acrylic fluorinated emulsion film formers including Foraperle® film formers such as Foraperle® 303 D from Elf Atochem (although Foraperle® may not be preferable for some cosmetic formulations); GANEX® copolymers such as butylated PVP, PVP/Hexadecene copolymer, PVP/Eicosene copolymer or tricontanyl; Poly(vinylpyrrolidone/diethylaminoethyl methacrylate) or PVP/Dimethylaminoethylmethacrylate copolymers such as Copolymer 845; Resin ACO-5014 (Imidized IB/MA copolymer); other PVP based polymers and copolymers; alkyl cycloalkylacrylate copolymers (See WO 98/42298, the disclosure of which is hereby incorporated by reference); Mexomere® film formers and other allyl stearate/vinyl acetate copolymers (allyl stearate/VA copolymers); polyolprepolymers such as PPG-12/SMDI copolymer, polyolprepolymers such as PPG-1 2/SM DI copolymer, Poly(oxy-1,2-ethanediyl), α-hydro-ω-hydroxy-polymer with 1,1'-methylene-bis-(4-isocyanatocyclohexane) available from Barnet; Avalure™ AC Polymers (Acrylates Copolymer) and Avalure™ UR polymers (Polyurethane Dispersions), available from BFGoodrich.

The at least one additional film former which also may be used within the framework of the invention includes film formers having any film former chemistry known in the art such as: PVP, acrylates, and urethanes; synthetic polymers of the polycondensate type or free-radical type, or ionic type, polymers of natural origin and mixtures thereof or any other film former known within the practice of the cosmetic and pharmaceutical arts which one skilled in the art may determine to be compatible.

The preferred concentration of the at least one additional film former may be determined by one of skill in the art and can vary considerably based on the application. For example, for cosmetic compositions, at least one additional film former may be used in an amount from 0% to 20% by weight, relative to the total weight of the composition.

The composition of the present invention may also further comprise at least one suitable additive commonly used in the field concerned chosen from water optionally thickened aqueous-phase thickener, water optionally gelled with a gelling agent, dyestuffs, antioxidants, essential oils, preserving agents, fragrances, fillers, pasty fatty substances, waxy fatty substances, neutralizing agents, liposoluble polymers, and cosmetically active agents and dermatological active agents such as, for example, emollients, moisturizers, vitamins, essential fatty acids and sunscreens.

In one embodiment, the at least one suitable additive is chosen from a wax. As used herein, a "wax" may be any lipophilic fatty compound. Non-limiting examples of such waxes include waxes of natural origin, such as beeswax, carnauba wax, candelilla wax, ouricury wax, Japan wax, cork fiber wax, sugar cane wax, paraffin waxes, lignite wax, microcrystalline waxes, lanolin wax, montan wax and ozokerites, hydrogenated oils such as hydrogenated jojoba oil, jojoba esters, waxes of synthetic origin, such as polyethylene waxes derived from polymerization of ethylene, waxes obtained by Fischer-Tropsch synthesis, fatty acid esters and glycerides, and silicone waxes such as derivatives of poly (di)methylsiloxane.

In one embodiment, the at least one additive is generally present, for example, in an amount ranging from 0% to 30% by weight of the total weight of the composition, such as from 0.3% to 9.3%.

Needless to say, the person skilled in the art will take care to select the optional additional additives and the amount thereof such that the advantageous properties of the composition according to the invention, such as thermal and mechanical stability and non-migration are not, or are not substantially, adversely affected by the addition(s) envisaged.

The invention also provides for a cosmetic delivery system comprising at least one linear dimethicone; at least one block copolymer film former chosen from tri-block copolymer film formers, multi-block copolymer film formers and radial block copolymer film formers; and at least one cosmetic powder.

In another embodiment, the invention provides a method of delivering a powder composition to a keratinous substance comprising applying to said keratinous substance a composition comprising at least one linear dimethicone; at least one block copolymer film former chosen from tri-block copolymer film formers, multi-block copolymer film formers and radial block copolymer film formers; and at least one cosmetic powder.

The invention will be illustrated by, but is not intended to be limited to, the following examples.

EXAMPLES

Example 1

A creme based makeup or foundation was prepared using the following ingredients:

| Phase | NAME | QTY |
|---|---|---|
| A | Jojoba Esters | 8 |
|   | Polyethylene | 2 |
| B | Dimethicone (Dow Corning 200/1.5 cst Fluid) | 2.5 |
| C | Titanium Dioxide | 9.2 |
|   | PTFE | 3.5 |
|   | Titanium Dioxide | 3.0 |
|   | Mica | 1.9 |
|   | Lauroyl Lysine | 0.1 |
|   | Aluminum Starch Octenylsuccinate | 2.0 |
|   | Isopropyl Titanium Triisostearate | 0.2 |
|   | Iron Oxides | 2.5 |
|   | Methylparaben | 0.1 |
| D | Cyclomethicone | 9.6 |
|   | Dimethicone (Dow Corning 200/1.5 cst Fluid) | 19.5 |
|   | Trimethylsiloxysilicate | 8.4 |
|   | Dimethiconol | 0.5 |
|   | Versagel M5960 | 2.0 |
|   | Preservatives | 0.3 |
|   | Lauryl PCA | 0.1 |
| E | Acrylates Copolymer | 0.9 |
|   | Isobutane | 0.1 |

The formulation was prepared using the following procedure. Phase C was pre-blended in a blender suitable for blending powders until the mixture was dispersed. Phase A was added to a suitable vessel and heated in an oil/steam bath at 90° C. until the phase was melted. The temperature was maintained at 90° C. throughout processing.

Phase B was added to phase A with stirring and the resultant was mixed until dispersed. Pre-blended phase C was added to the A/B mixture with stirring and the resulting composition was mixed until dispersed. Phase D was then added to the A/B/C mixture with stirring until the mixture was dispersed. Finally, phase E was added to the A/B/C/D mixture and the formulation was mixed until dispersed. The resulting mixture was used to fill a suitable container or mold and cooled.

Example 2

A creme based makeup or foundation, similar to the composition in Example 1, was prepared using the procedure of Example 1. The following composition, however, did not contain trimethylsiloxysilicate.

| Phase | NAME | QTY |
|---|---|---|
| A | Polyethylene | 2.0 |
|   | Jojoba Wax Flakes | 8.0 |
| B | Dimethicone (Dow Corning 200/1.5 cst Fluid) | 25 |
| C | PTFE | 3.5 |
|   | Titantium Dioxide (ITT Treated) | 12.7 |
|   | Mica | 1.9 |
|   | Aluminum Starch Octenylsuccinate (ITT Treated) | 2.0 |
|   | Red Bro - 101 (ITT Treated) | 0.6 |
|   | Yellow Byo - 201 (ITT Treated) | 1.1 |
|   | Methylparaben | 0.1 |
|   | Blue Bub 201 (ITT Treated) | 0.6 |
|   | Lauroyl Lysene | 0.1 |

-continued

| Phase | NAME | QTY |
|---|---|---|
| D | Dimethicone (Dow Corning 200/1.5 cst Fluid) | 38.8 |
|   | Parabens | 0.4 |
|   | Lauryl PCA | 0.3 |
|   | Versagel M5960 | 2.0 |
| E | Acrylates Copolymer | 1 |

Example 3

A makeup formulation was prepared with the following ingredients using the procedure of Example 1.

| | | |
|---|---|---|
| A) | Polyethylene | 2 |
|   | Jojoba wax flakes | 8 |
| B) | Dimethicone (Dow Corning 200/1.5 cst Fluid) | 25 |
| C) | PTFE | 3.5 |
|   | Titanium Dioxide (ITT Treated) | 13.5 |
|   | Mica | 2.0 |
|   | Starch ASO-I2 (ITT Treated) | 2.0 |
|   | Red Bro - 101 (ITT Treated) | 0.5 |
|   | Yellow Byo 201 (ITT Treated) | 1.1 |
|   | Black Bbo-I2 (ITT Treated) | 0.3 |
|   | Methylparaben | 0.1 |
| D) | Trimethylsiloxysilicate in cyclomethicone (GE SS4230) | 22.0 |
|   | Dimethicone (Dow Corning 200/1.5 cst Fluid) | 16.8 |
|   | Parabens | 0.4 |
|   | Lauryl PCA | 0.3 |
|   | Versagel M5960 | 2.0 |
| E) | Acrylates Copolymer | 1 |
|   |   | 100% |

Example 4

The formulations of Examples 1 and 2 were evaluated by a transfer resistance test. A transfer resistance test is used to evaluate the transfer resistant properties of a composition using a fabric.

The composition of each example was applied to the clean, bare skin of 15 women as a smooth, thin layer that was at minimum 1"×1" square in size. Since these products were in a compact form instead of a liquid form, a non-latex sponge was wiped across the foundation in compact form (approximately 20 times) to obtain sufficient product to adequately cover the treated area.

The product was allowed to air dry for 5 minutes and using a facial tissue and medium pressure the area was wiped as if attempting to wipe the product off of the skin. The 15 subjects were then asked to evaluate the results. Positive results were described as the presence of a makeup film that could not be easily removed without soap and water. The results were rated on a scale of 1 to 5 with 5 being the best and 1 being the worst. To be considered transfer-resistant, a formulation should have a median rating of greater than or equal to 4. The compositions of Example 1 and 2 both had an average rating of 5.

A similar procedure was used to test the transfer resistance of the formulation of Example 3. In place of a tissues, a test fabric made of 100% cotton was used to wipe the area where the formulation was applied. Both the Gray Scale and Product Deposit Scale were used to evaluate the formulation. The Gray Scale is a standard for evaluating staining of unstained textiles resulting from colorfastness tests (ISO International Standard 105-A03). The Product Deposit Scale refers to the following results, which are judged with the naked eye: 1—No product was deposited; 2—Slight amounts were deposited; 3—Moderate amounts were deposited; and 4—Heavy amounts were deposited.

To be considered transfer-resistant, a formulation should have a median rating of greater than or equal to 4, according to the Gray Scale and a median rating of greater than or equal to 2, according to the Product Deposit scale. The formulation of Example 3 received a rating of 4.5 on the Gray Scale and 2.0 on the Product Deposit Scale. Thus, the formulation was found to be transfer resistant.

It will be apparent to those skilled in the art that various modifications and variations can be made in the compositions and methods of the present invention without departing from the spirit or scope of the invention. Thus, it is intended that the present description cover the modifications and variations of this invention provided that they come within the scope of the appended claims and their equivalents.

What is claimed is:

1. A composition comprising:
   at least one linear dimethicone; and
   at least one block copolymer film former chosen from tri-block copolymer film formers, multi-block copolymer film formers and radial block copolymer film formers,
   with the proviso that said composition comprises at least one tri-block copolymer film former,
   wherein said at least one block copolymer film former is present in an amount ranging from 0.139% to 1.953% by weight relative to the total weight of the composition; and
   said at least one linear dimethicone is present in an amount ranging from 25% to 75%.

2. The composition according to claim 1, wherein said at least one linear dimethicone is chosen from linear polydimethylsiloxanes of the formula

$(CH_3)_3Si\text{—}O\text{—}(\text{—}Si(CH_3)_2\text{—}O\text{—})_n\text{—}Si(CH_3)_3$ wherein n ranges from 0 to 7.

3. The composition according to claim 1, wherein said at least one linear dimethicone is chosen from dimethicone copolyols, dimethicone silylate, and dimethicone propylethylenediamine behenate.

4. The composition according to claim 3, wherein said dimethicone copolyols are chosen from dimethicone copolyol acetate, dimethicone copolyol adipate, dimethicone copolyol almondate, dimethicone copolyolamine, dimethicone copolyol butyl ether, dimethicone copolyol laurate, and dimethicone copolyol stearate.

5. The composition according to claim 1, wherein said at least one block copolymer film former comprises at least one hard block copolymer segment chosen from styrenes and at least one soft block copolymer segment chosen from ethylene, propylene, and butylene.

6. The composition according to claim 1, wherein said at least one triblock copolymer film former is a linear A-B-A block chosen from styrene-butadiene-styrene, styrene-isoprene-styrene, and styrene-ethylenebutylene-styrene.

7. The composition according to claim 1, wherein said at least one triblock copolymer film former is a styrene/butylene/ethylene/styrene copolymer.

8. The composition according to claim 1, wherein said at least one radial block copolymer film former is an ethylene/propylene/styrene copolymer.

9. The composition according to claim 1, wherein said at least one block copolymer film former is present in said composition in an amount ranging from 0.265% to 1.953% by weight.

10. The composition according to claim 1, wherein said at least one linear dimethicone is present in said composition in an amount ranging from 42% to 54% by weight.

11. The composition according to claim 1, further comprising at least one powder.

12. The composition according to claim 11, wherein said at least one powder is chosen from solid polymers and vegetable flours.

13. The composition according to claim 12, wherein said solid polymers are chosen from polyethylene, PTFE, acrylates copolymer, ethylene acrylate copolymer, PMMA and polyvinylidene copolymer.

14. The composition according to claim 11, wherein said at least one powder material is present in said composition in an amount ranging from 0.1% to 50% by weight.

15. The composition according to claim 1, further comprising at least one cyclic dimethicone.

16. The composition according to claim 1, further comprising at least one silicone resin which is different than said at least one linear dimethicone.

17. The composition according to claim 16, wherein said at least one silicone resin which is different than said at least one linear dimethicone is chosen from siloxanes, siloxysilicates and silsesquioxanes.

18. The composition according to claim 17, wherein said siloxane is a polydimethylsiloxane.

19. The composition according to claim 17, wherein said silsesquioxanes is chosen from polymethylsilsesquioxanes.

20. The composition according to claim 17, wherein said siloxysilicates is chosen from trimethylsiloxysilicates.

21. The composition according to claim 1, wherein said composition further comprises at least one additional ingredient chosen from pigments, sunscreens, and skin protectant coatings.

22. The composition according to claim 1, wherein said composition is in the form of an eyeshadow, eyeshadow base, blush, lipstick, fragrance delivery system, deodorant stick, skin protectant stick, sunscreen stick, medication cream, adhesive or insect repellent.

23. The composition according to claim 1, further comprising at least one additional film former.

24. The composition according to claim 23, wherein said at least one additional film former is present in said composition in an amount ranging from 0% to 20% by weight.

25. The composition according to claim 1, further comprising at least one wax.

26. The composition according to claim 11, wherein said at least one powder is chosen from pigments, fillers, and pearling agents.

27. The composition according to claim 11, wherein said at least one powder is chosen from talc, nylons, silicas, silks, and starches.

28. A cosmetic delivery system comprising
   at least one linear dimethicone;
   at least one block copolymer film former chosen from tri-block copolymer film formers, multi-block copolymer film formers and radial block copolymer film formers; and
   at least one cosmetic powder,
   with the proviso that said cosmetic delivery system comprises at least one tri-block copolymer film former, wherein said at least one block copolymer film former is present in an amount ranging from 0.139% to 1.953% by weight relative to the total weight of the composition; and said at least one linear dimethicone is present in an amount ranging from 25% to 75%.

29. A method of delivering a powder composition to a keratinous substance comprising applying to said keratinous substance a composition comprising at least one linear dimethicone;

at least one block copolymer film former chosen from tri-block copolymer film formers, multi-block copolymer film formers and radial block copolymer film formers; and at least one cosmetic powder, wherein said at least one block copolymer film former is present in an amount ranging from 0.139% to 1.953% by weight relative to the total weight of the composition; and said at least one linear dimethicone is present in an amount ranging from 25% to 75%.

30. A composition comprising:

at least one linear dimethicone;

at least one block copolymer film former chosen from tri-block copolymer film formers, multi-block copolymer film formers and radial block copolymer film formers, and at least one cyclic dimethicone, with the proviso that said composition comprises at least one tri-block copolymer film former, wherein said at least one block copolymer film former is present in an amount ranging from 0.139% to 1.953% by weight relative to the total weight of the composition; and said at least one linear dimethicone is present in an amount ranging from 25% to 75%.

31. A composition comprising:

at least one linear dimethicone in an amount ranging from 25% to 75% by weight relative to the total weight of the composition; and at least one block copolymer film former chosen from tri-block copolymer film formers, multi-block copolymer film formers and radial block copolymer film formers, with the proviso that said composition comprises at least one tri-block copolymer film former, wherein said at least one block copolymer film former is present in an amount ranging from 0.139% to 1.953% by weight relative to the total weight of the composition.

* * * * *